(12) United States Patent
Blankenberg et al.

(10) Patent No.: US 7,357,915 B2
(45) Date of Patent: Apr. 15, 2008

(54) METHOD OF IMAGING CELL DEATH IN VIVO

(75) Inventors: Francis G. Blankenberg, Menlo Park, CA (US); H. W. Strauss, Redwood City, CA (US); Jonathan F. Tait, Seattle, WA (US); Peter D. Katsikis, Secane, PA (US)

(73) Assignees: The Board of Trustees of the Leland Stanford Junior University, Stanford, CA (US); University of Washington, Seattle, WA (US)

( * ) Notice: Subject to any disclaimer, the term of this patent is extended or adjusted under 35 U.S.C. 154(b) by 526 days.

(21) Appl. No.: 10/210,986

(22) Filed: Aug. 2, 2002

(65) Prior Publication Data

US 2007/0243133 A1    Oct. 18, 2007

Related U.S. Application Data

(63) Continuation of application No. 09/643,689, filed on Aug. 22, 2000, now abandoned, which is a continuation of application No. 09/069,878, filed on Apr. 29, 1998, now Pat. No. 6,197,278.

(60) Provisional application No. 60/045,399, filed on Apr. 30, 1997.

(51) Int. Cl.
*A61K 51/08* (2006.01)
*A61K 49/00* (2006.01)
*A61K 103/00* (2006.01)
*G01N 33/567* (2006.01)
*G01N 33/532* (2006.01)

(52) U.S. Cl. ............... 424/1.69; 424/1.11; 424/9.1; 436/504; 436/544; 436/545; 436/57; 436/58

(58) Field of Classification Search .............. None
See application file for complete search history.

(56) References Cited

U.S. PATENT DOCUMENTS

| | | | |
|---|---|---|---|
| 4,671,256 A | 6/1987 | Lemelson | |
| 5,519,221 A | 5/1996 | Weinberg | |
| 5,552,525 A | 9/1996 | Dean | |
| 5,627,036 A | 5/1997 | Reutelingsperger | |
| 5,632,986 A | 5/1997 | Tait et al. | |
| 5,776,427 A | 7/1998 | Thorpe et al. | 424/1.49 |
| 5,855,866 A | 1/1999 | Thorpe et al. | 424/1.49 |
| 5,863,538 A | 1/1999 | Thorpe et al. | 424/136.1 |
| 5,955,437 A | 9/1999 | Reutelingsperger | 514/21 |
| 5,965,132 A | 10/1999 | Thorpe et al. | 424/149 |
| 5,968,477 A * | 10/1999 | Kasina et al. | 424/1.69 |
| 6,004,554 A | 12/1999 | Thorpe et al. | 424/178.1 |
| 6,051,230 A | 4/2000 | Thorpe et al. | 424/178.1 |
| 6,261,535 B1 | 7/2001 | Thorpe et al. | 424/1.49 |
| 6,312,694 B1 | 11/2001 | Thorpe et al. | 424/178.1 |
| 6,406,693 B1 | 6/2002 | Thorpe et al. | 424/130.1 |

FOREIGN PATENT DOCUMENTS

| | | |
|---|---|---|
| WO | WO 92/19279 A1 | 11/1992 |
| WO | WO 94/10149 A1 | 5/1994 |
| WO | WO 95/27903 A1 | 10/1995 |
| WO | WO 95/34315 * | 12/1995 |
| WO | WO 95/34315 A1 | 12/1995 |
| WO | WO 96/17618 A1 | 6/1996 |
| WO | WO 98/04294 A2 | 2/1998 |
| WO | WO 98/04294 A3 | 2/1998 |
| WO | WO 00/02584 A2 | 1/2000 |
| WO | WO 00/02584 A3 | 1/2000 |
| WO | WO 00/02587 A1 | 1/2000 |

OTHER PUBLICATIONS

Delpassand et al J. Pharm. Sci. 1996; 85(6):553-559.*
Ravanat C. et al Biochem J. Feb. 15, 1992;282 ( Pt 1):7-13.*
Liu et al (Bioconjugate Chem 1996; 7:63-71).*
Edwards et al (Bioconjugate Chem 1997;8:146-154).*
Goodman et al (The Pharmacological Basis of Therapeutics; 1980, Macmillan Publishing Co.,Inc. pp. 1-27).*
Shih et al (Clin Nucl Med. Nov. 1993;18(11):945-9).*
Blankenberg et al. "Increased localization of TC-99m hydrazino nicotinamide (HYNIC) labeled annexin V lipocortin in lymphatic tissue of animals treated with dexamethazone." *J. Nuc. Med.* 1997;38(5):268P.
Blankenberg et al. "Quantitative analysis of apoptotic cell death using proton nuclear magnetic resonance spectroscopy." *Blood* May 15, 1997;89(10):3778-86.
Kasina et al. "Preformed chelate TC-99m radiolabeling of r-annexin V for arterial thromnus imaging." *J. Nuc. Med.* 1996;37(5):29.
Stratton et al. "Selective uptake of radiolabeled annexin V on acute porcine left atrial thrombi." *Circulation* Nov. 15, 1995;92(10):3113-21.
Babich, J.W., et al., "Technetium-99m-Labeled Hydrazino Nicotinamide Derivatized Chemotactic Peptide Analogs for Imaging Focal Sites of Bacterial Infection," *The Journal of Nuclear Medicine* 34(11):1964-1974 (1993).
Barrow, S.A., et al., "Localization of Indium-111-Immunoglobulin G, Technetium-99m-Immunoglobulin G and Indium-111-Labeled White Blood Cells at Sites of Acute Bacterial Infection in Rabbits," *The Journal of Nuclear Medicine* 34:1975-1979 (1993).
Bennett, M.R., et al., "Binding and Phagocytosis of Apoptotic Vascular Smooth Muscle Cells Is Mediated in Part by Exposure Phosphatidylserine," *Circ. Res.* 77:1136-1142 (1995).

(Continued)

*Primary Examiner*—Christopher H. Yaen
(74) *Attorney, Agent, or Firm*—Giulio A. DeConti, Jr.; Maria Laccotripe Zacharakis

(57) ABSTRACT

A method of imaging apoptosis in vivo, using radiolabeled annexin, is described.

60 Claims, 3 Drawing Sheets

OTHER PUBLICATIONS

Blankenberg, F.G., et al., "Detection of Apoptotic Cell Death by Proton Nuclear Magnetic Resonance Spectroscopy," *Blood* 87(5):1951-1956 (1996).

Koopman, G., et al., "Annexin V for Flow Cytometric Detection of Phosphatidylserine Expression on B Cells Undergoing Apoptosis," *Blood* 84(5): 1415-1420 (1994).

Reutelingsperger, C.P.M., and W.L. van Heerde, "Annexin V, the regulator of phosphatidylserine-catalyzed inflammation and coagulation during apoptosis," *Cell. Mol. Life Sci.* 53:527-532 (1997).

Schwartz, David A., et al. "Preparation of Hydrazino-Modified Proteins and Their Use for the Synthesis of .sup.99m Tc-Protein Conjugates," *Bioconjugate Chem.* 2: 333-336 (1991).

Tait, J.F., and C. Smith, "Site-Specific Mutagenesis of Annexin V:Role of Residues from Arg-200 to Lys-207 in Phospholipid Binding," *Archives of Biochem. and Biophys.* 288(1):141-144 (1991).

Tait, J.F., and D. Gibson, "Measurement of membrane phospholipid asymmetry in normal and sickle-cell erthrocytes by means of annexin V binding," *J.Lab. Clin. Med.* 123:741-748 (1994).

Tait, J.F., et al., "Phospholipid Binding Properties of human Placental Anticoagulant Protein-I, a Member of the Lipocortin Family," *The Journal of Biological Chemistry* 264(14):7944-7949 (1989).

Tait, J.F., et al., "Placental Anticoagulant Proteins: Isolation and Comparative Characterization of Four Members of the Lipocotrin Family," *Biochemistry* 27:6268-6276 (1988).

Tait, Jonathan F., "Clinical Applications of Annexins," *Annexins:Molecular Structure to Cellular Function*, ed. Barbara A. Seaton, R.G. Landes Co., 1996, pp. 213-220.

van Heerde, W.L., et al., "The Complexity of the Phospholipid Binding Protein Annexin V," *Thrombosis and Haemostasis* 73(2):172-179 (1995).

Wood, B.R., et al., "Increased Erythrocyte Phosphatidylserine Exposure in Sickle Cell Disease: Flow-Cytometric Measurement and Clinical Associations," *Blood* 88(5): 1873-1880 (1996).

Zwaal, Robert F.A., and Alan J. Schroit, "Pathophysiologic Implications of Membrane Phospholipid Asymmetry in Blood Cells," *Blood* 89(15): 1121-1132 (1997).

* cited by examiner

METHOD OF IMAGING CELL DEATH IN VIVO

This application claims the priority of U.S. Provisional Application No. 60/045,399 filed Apr. 30, 1997, which is incorporated herein by reference. This application is a continuation of U.S. application Ser. No. 09/643,689 filed Aug. 22, 2000, now abandoned, which is a continuation of U.S. application Ser. No. 09/069,878 filed Apr. 29, 1998, which issued on Mar. 6, 2001, as U.S. Pat. No. 6,197,278.

FIELD OF THE INVENTION

The present invention relates to a method of imaging cell death in vivo. In particular, it relates to the use of radiolabeled annexin to image regions of cell death in a mammal using gamma ray imaging.

REFERENCES

Amann, E. and Brosius, J., *Gene* 40:183 (1985).
Asselin, B. L., et al., *Cancer Res.* 49:4363 (1989).
Ausubel, F. M., et al., *Current Protocols in Molecular Biology* (John Wiley and Sons, Inc., Media, P A).
Babich, J. W., et al., *Journal of Nuclear Medicine* 34:1964 (1993).
Ballon, D., et al., *Magn. Reson. Med.* 19:85 (1991).
Barrow, S. A., et al., *J. Nucl. Med.* 34:1975 (1993).
Beames, et al., *Biotechniques* 11:378 (1991).
Bindl, J. M. & Warnke, R. A., *Am. J. Clin. Pathol.* 85:490-493 (1986).
Blankenberg, F. G., et al., *Blood* 87:1951 (1996).
Borenstain-Ben Yashar, V., et al., *Am. J. Hematol.* 44:63 (1993).
Connor, J., et al., *J. Biol. Chem.* 267:19412 (1992).
D'Amico, A. V., and McKenna, W. G., *Radiotherapy and Oncology* 33:3 (1994).
Darzynkiewicz, Z., J. of *Cell Biochem.* 58:151 (1995).
Darzynkiewicz, Z., et al., *Methods in Cell Biology* 41:15 (1994).
Dive, C., et al., *Biochim et Biophys Acta* 1133:275 (1992).
Du, C., et al., *J. Cereb. Blood Flow and Metab.* 16: 195-201 (1996).
Fadok, V. A., et al., *J. of Immunol.* 148:2207 (1992).
Fadok, V. A., et al., *J. of Immunol.* 149:4029 (1992).
Fadok, V. A., et al., *J. of Immunol.* 151:4274 (1993).
Fischman, et al., *J. Nucl. Med.* 32:482-491 (1991).
Funakoshi, T., et al., *Biochemistry* 26:5572 (1987).
Funk, G. M., et al., *J. Lipid Res.* 27:792 (1986).
Gavrieli, Y., et al., *J. Cell Biol.* 119:493 501 (1992).
Geng, Y.-J., et al., *Arteriosclerosis, Thrombosis, and Vascular Biol.* 15:1995 (1995).
Harlow, E., et al., ANTIBODIES: A LABORATORY MANUAL, Cold Spring Harbor Laboratory Press (1988).
Hnatowich, D. J., et al., *J. Immunol. Meth.* 65:147 (1983).
Jensen, K. E., et al., *Magr'. Reson. Imaging* 8:779 (1990).
Koopman, G., et al., *Blood* 84(5):1415-1520 (1994).
Lacronique, V., et al., *Nature Med.* 2(1):80 (1996).
LaMuraglia, et al., *J. Vasc. Surg.* 10:20-28 (1989).
Lane, A., et al., *Am. J. Hematol.* 47:295 (1994).
Larson, S. K., et al., *Biocor~jugate Chem.* 6:635-638 (1995).
Lind, et al., *J. Nucl. Med.* 31:417-473 (1990).
Maloney, D. G., et al., *Hybridoma* 4:191-209 (1985).
Martin, S. J., et al., *J. Exp. Med.* 182:1545 (1995).
May, G. L., et al., *J. Biochem.* 261:3048 (1986).
Mettler, F. A. and M. J. Guiberteau, ESSENTIALS OF NUCLEAR MEDICINE IMAGING, Second Edition, W.B. Saunders Company, Philadelphia, Pa. (1985).
Mirkovic, N., et al., *Radiotherapy and Oncology* 33:11 (1994).
Mitchell, K. T., et al., *Anal. Biochem.* 158:447 (1986).
Mombers, C., et al., *Biochem et Biophys Acta* 551:271 (1979).
Mountford, C. E., and Tattersall, M. H. N., *Cancer Surv.* 6:285 (1987).
Mulkem, R. V., et al., *J. Magn. Reson. Imaging* 4:585 (1994).
Mullis, K. B., et al., U.S. Pat. No. 4,683,195, issued 28 Jul. 1987.
Mullis, K. B., U.S. Pat. No. 4,683,202, issued 28 Jul. 1987.
Narula, J., et al., *New Engl. J. Med.* 335:1182 (1996).
Naumovski, L., and Cleary, M. L., *Blood* 83:2261 (1994).
Niemeyer, C. M., et al., (*Protocol* 81-01 Update) *Blood* 78:2514 (1991).
Ogasawara, J., et al., *Nature* 364:806 (1993).
Pak, C. C. and I. J. Fidler, *Semin. Cancer Biol.* 2:189 (1991).
Perillo, N. L., et al., *Nature* 378:736 (1995).
Reilly, P. R., et al., in BACULOVIRUS EXPRESSION VECTORS: A LABORATORY MANUAL (1992).
Rodriguez, I., et al., *J. Exp. Med.* 184:2067-2072 (1996).
Sambrook, J., et al., MOLECULAR CLONING: A LABORATORY MANUAL, Second Edition, Cold Spring Harbor Laboratory, Cold Spring Harbor, N.Y. (1989).
Schick, F., et al., *Magn. Reson. Med.* 26:207 (1992).
Schwartz, D. A., et al., *Bioconjugate Chem.* 2:333 (1991).
Seigneuret, M., and P. F. Devaux, *Proc. National Acad. Sci. USA* 81:3751 (1984).
Seiter, K., et al., *Leukemia* 2:1961 (1995).
Smith, D. B., et al., *Gene* 67:31 (1988).
Stark, R. E., et al., *J. of Physical Chemistry* 89:272 (1985).
Stark, R. E., et al., *Biochemica et Biophysica Acta* 860:399 (1986).
Stephens, L. C., et al., *Radiation Res.* 135:75 (1993).
Stratton, J. R., et al., *Circulation* 92:3113-3121 (1995).
Tait, J. F., "Clinical Applications of Annexins," in ANNEXINS: MOLECULAR STRUCTURE TO CELLULAR FUNCTION (Seaton, B. A., Ed.) R. G. Landes Company (1996).
Tait, J. F. and Gibson, D., *J. Lab. Clin. Med.* 123:741 (1994).
Tait, J. F. and Smith, C., *Arch. Biochem. Biophys.* 288:141 (1991).
Tait, J. F., et al., *J. Biol. Chem.* 264:7944 (1989).
Tait, J. F., et al., *Biochem* 27:6268 (1988).
Thompson, C. B., *Science* 267:1456 (1995).
Verhoven, B., et al., *J. Experimental Med.* 182:1597 (1995).
Wang, Z. Q., et al., *European Journal of Immunology* 24:1549 (1994).
Williamson, P., and Schleel, R. A., *Molecular Membrane Biology* 11:199 (1994).
Wood, B. L., et al., *Blood* 88:1873-1880 (1996).
Woodley, S. L., et al., *Transplantation* 56:1443-1447 (1993).
Young, T. L. & Santella, R. M., *Carcinogenesis* 9:589-592 (1988).
Zwaal, R. F. A., and Schroit, A. J., *Blood* 89(4):1121-1132 (1997).
Zwaal, R. F. A., et al., *Biochem. Soc. Trans.* 21:248 (1993).

BACKGROUND OF THE INVENTION

Apoptotic or programmed cell death plays a crucial role in development and a number of homeostatic and disease processes (Thompson, 1995). New therapeutic strategies of a variety of diseases may therefore be possible through the modulation of apoptotic cell death. The study of new pharmacologic agents to promote or inhibit apoptotic cell death has been impeded by the lack of a non-invasive method(s) to detect and monitor apoptotic cell death in vivo.

Lipid proton nuclear magnetic resonance spectroscopy ($^1$H NMRS) has been found to be useful in the detection of the specific changes of composition and/or fluidity of the plasma membrane of lymphoblasts and other cell lines undergoing apoptotic cell death (Blankenberg, et al., 1996). Clinical use of lipid $^1$H NMRS study apoptosis is currently limited by complex local magnetic microenvironments found naturally in many tissues and organs.

SUMMARY OF THE INVENTION

In one aspect, the present invention includes a method of imaging cell death (e.g., cell death due to apoptosis or necrosis) in a region of a mammalian subject in vivo. The method includes the steps of (a) administering to the subject, annexin labelled with a biocompatible radionuclide, (b) after a period of time in which the labeled annexin can achieve localization in the subject, positioning the subject within the detection field of a radiation detector device, and (c) measuring radiation emission from the radionuclide localized in the subject, with the radiation detector device, to construct an image of radiation emission, where the image is a representation of cell death in the region of the mammalian subject. In one embodiment, the method further includes a step (d) of processing the image to subtract signal resulting from non-specific localization of the labeled annexin, such as non-specific localization in the kidney.

Radionuclides useful with the method include Iodine 123, Iodine 131, Gallium 67, Indium 111, Fluorine 18, and Technetium 99 m (Tc99m). It will be appreciated that Fluorine 18 is a positron emitter, and is thus useful in positron emission tomography (PET). Iodine 123, Iodine 131, Gallium 67, Indium 111, and Technetium 99 m are useful with standard gamma emission detection. Tc99m is a preferred radionuclide for use with the methods of the invention. In a preferred embodiment, the Tc99m is linked to the annexin via hydrazino nicotinamide (HYNIC). Tc99m-labelled annexin is typically administered at a dose of between about 5 and about 20 mCi.

In one general embodiment of the invention, the radiation detector device is a gamma ray detector device and the measured radiation emission is gamma ray emission. In another general embodiment, the radiation detector device is a positron emission detector device and the measured radiation emission is positron emission.

In yet another general embodiment, the method further includes repeating steps (b) and (c) at selected intervals, where the repeating is effective to track changes in the intensity of radiation emission (e.g., gamma ray or positron emission) from the region over time, reflecting changes in the number of cells undergoing cell death.

Still another general embodiment includes repeating steps (b) and (c) at selected intervals, where the repeating is effective to track changes in the localization of gamma ray emission in the region over tune, reflecting changes in the location of cells undergoing cell death.

The radiation detector device may be, for example, an Anger gamma scintillation camera or a 3-dimensional imaging camera.

A preferred annexin for use with the invention is annexin V. It is typically administered at doses less than about 300 μg protein/kg, preferably between about 1 and 10 μg protein/kg.

Several administration routes are possible, including intravenous (i.v.), intrapentoneal (i.p.), intrathecal, and intrapleural administration.

The measuring of gamma ray emission to construct an image is typically done between about 5 minutes and about 2 hours after administration of the labelled annexin. In one embodiment, the measuring of gamma ray emission to construct the image is done about 1 hour after administration of the labelled annexin.

Different portions of the subject may be imaged using the method disclosed herein. For example, the region may include substantially the whole subject, or a portion of the subject, such as the head or portion thereof, the heart or portion thereof, the liver or portion thereof, and the like.

The invention also provides a kit for imaging cell death in vivo. The kit includes (i) a sealed vial containing HYNIC-labeled annexin, prepared, for example, as described in Materials and Methods (A), (ii) a sealed vial containing a Sn-tricine solution prepared, for example, as described in Materials and Methods (B), and maintained under $N_2$, (iii) instructions for making Tc-99m labeled annexin using the components of (i) and (ii) along with Tc-99m, and (iv) instructions for administering the Tc-99m annexin to image areas of cell death in vivo. In one embodiment, the kit is maintained at −70° C. and shipped on dry ice. In another embodiment, the HYNIC-labeled annexin is lyophilized.

These and other objects and features of the invention will become more fully apparent when the following detailed description is read in conjunction with the accompanying drawings.

DETAILED DESCRIPTION OF THE INVENTION

I. Definitions

Figure 1:
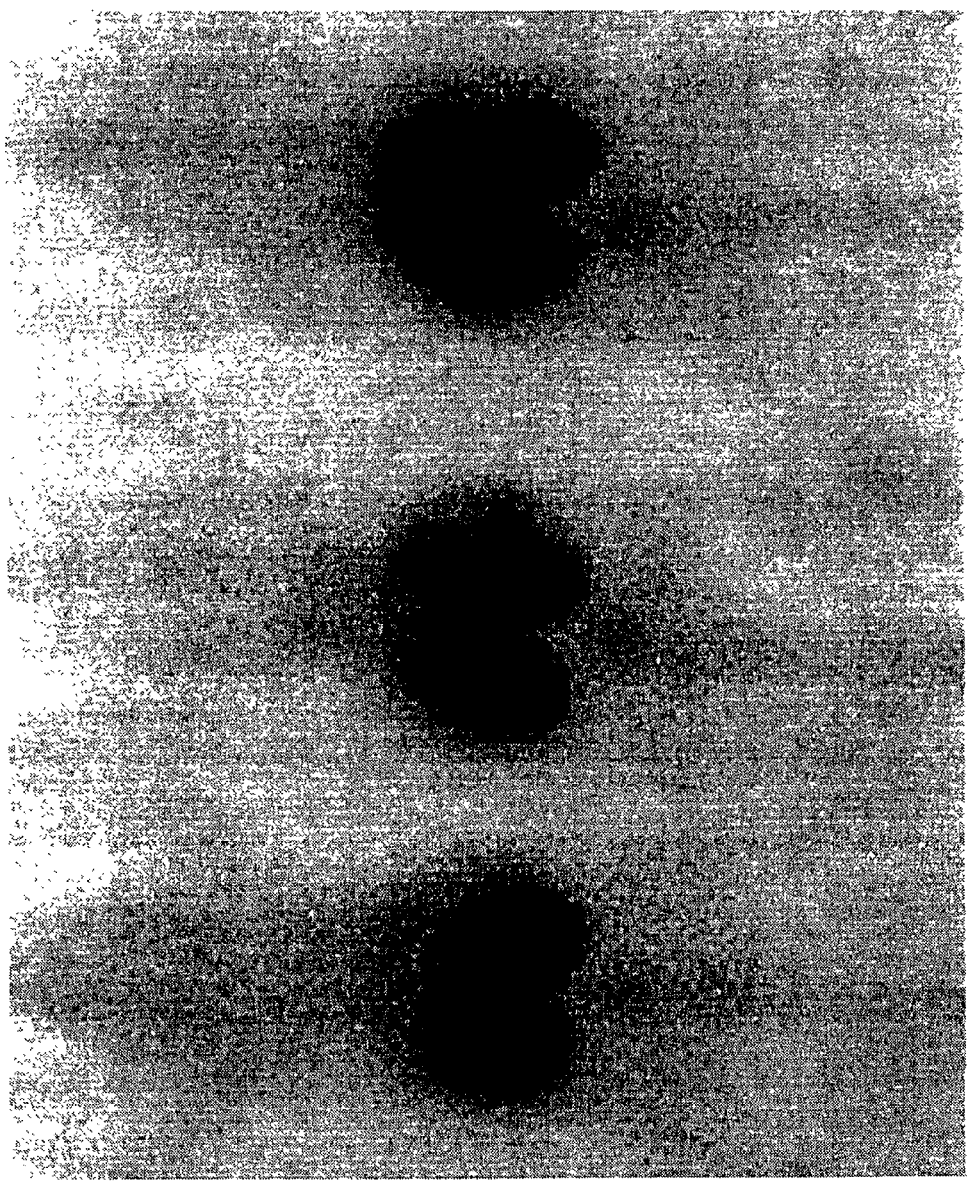
FIG. 1 is a computer-generated image showing Fas-mediated fulminant hepatic apoptosis as detected with Tc99m HYNIC-annexin V.

The term "cell death" in the context of "detecting cell death" or "localizing cell death" refers to cells that have lost plasma membrane integrity, as well as to the processes by which mammalian cells die. Such processes include apoptosis and processes thought to involve apoptosis (e.g., cell senescence), as well as necrosis. "Cell death" is used herein to refer to the death or imminent death of nucleated cells (e.g., neurons, myocytes, hepatocytes, etc.) as well as to the death or imminent death of anucleate cells (e.g., red blood cells, platelets, etc.).

A "biocompatible radionuclide" or "biocompatible radioisotope" is an isotope that is recognized as being useful for injection into a patient for nuclear medicine applications. Examples of biocompatible radionuclides include Iodine 123, Iodine 131, Gallium 67, Indium 111, Fluorine 18 and Technetium 99m.

II. Cell Death—Apoptosis and Necrosis

Apoptosis refers to "programmed cell death" whereby the cell executes a "cell suicide" program. It is now thought that the apoptosis program is evolutionarily conserved among virtually all multicellular organisms, as well as among all the cells in a particular organism. Further, it is believed that in many cases, apoptosis may be a "default" program that must be actively inhibited in healthy surviving cells.

The decision by a cell to submit to apoptosis may be influenced by a variety of regulatory stimuli and environmental factors (Thompson, 1995). Physiological activators of apoptosis include tumor necrosis factor (TNF), Fas ligand, transforming growth factor β, the neurotransmitters glutamate, dopamine, N-methyl-D-aspartate, withdrawal of growth factors, loss of matrix attachment, calcium and glucocorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation (antimetabolites). Therapy-associated apoptosis inducers include gamma radiation, UV radiation and a variety of chemotherapeutic drugs, including cisplatin, doxorubicin, bleomycin, cytosine arabinoside, nitrogen mustard, methotrexate and vincristine. Toxin-related inducers of apoptosis include ethanol and β-amyloid peptide.

Apoptosis can have particularly devastating consequences when it occurs pathologically in cells that do not normally regenerate, such as neurons. Because such cells are not replaced when they die, their loss can lead to debilitating and sometimes fatal dysfunction of the affected organ. Such dysfunction is evidenced in a number of neurodegenerative disorders that have been associated with increased apoptosis, including Alzheimer's disease, Parkinson's disease, amyotrophic lateral sclerosis, retinitis pigmentosa and cerebellar degeneration.

The consequences of undesired apoptosis can be similarly devastating in other pathologies as well, including ischemic injury, such as typically occurs in cases of myocardial infarction, reperfusion injury and stroke. In particular, apoptosis is believed to play a central role in very delayed infarction after mild focal ischemia (Du, et al., 1996). Additional diseases associated with increased apoptosis include, but are not limited to, the following: AIDS; myelodysplatic syndromes, such as aplastic anemia; and toxin-induced liver disease, including damage due to excessive alcohol consumption.

Necrosis is the localized death of cells or tissue due to causes other than apoptosis (i.e., other than the execution of the cell's intrinsic suicide program). Necrosis can be caused by traumatic injury, bacterial infection, acute hypoxia and the like. There is some overlap between the two types of cell death, in that some stimuli can cause either necrosis or apoptosis or some of both, depending on the severity of the injury.

III. Asymmetry of Biological Membranes

It is generally believed that biological membranes are asymmetric with respect to specific membrane phospholipids. In particular, the outer leaflet of eukaryotic plasma membranes is formed predominantly with the cholinephospholipids, such as sphingomyelin and phosphatidylcholine (PC), whereas the inner leaflet contains predominantly aminophospholipids, such as phosphatidylserine (PS) and phosphatidyletanolamme (PE). This asymmetry is thought to be maintained by the activity of an adenosine triphosphate (ATP)-dependent aminophospholipid translocase, which selectively transports PS and PE between bilayer leaflets (Seigneuret and Devaux, 1984). Other enzymes thought to be involved in the transport of phospholipids between leaflets include ATP-dependent floppase (Connor, et al., 1992) and lipid scramblase (Zwaal, et al., 1993).

Although asymmetry appears to be the rule for normal cells, the loss of such asymmetry is associated with certain physiological, as well as pathogenic, processes. For example, it has been recognized that membrane asymmetry, detected as appearance of PS on the outer leaflet of the plasma membrane ("PS exposure"), is one of the earliest manifestations of apoptosis, preceding DNA fragmentation, plasma membrane blabbing, and loss of membrane integrity (Martin, et al., 1995; Fadok, et al., 1992).

Similar re-orientation has been observed in sickle cell disease (Lane, et al., 1994), β-thalassemia (Borenstain-Ben Yashar, et al., 1993), platelet activation, and in some mutant tumor cell lines with defective PS transport. A gradual appearance of PS on the outer leaflet has also been observed to occur in aging red blood cells (Tait and Gibson, 1994). When the PS exposure on such cells reaches a threshold level, the cells are removed from circulation by macrophages (Pak and Fidler, 1991). All of the above conditions proximately culminate in the death of the affected cells (i.e., cells with significant PS exposure).

It will be appreciated that PS exposure is a component in both apoptosis and necrosis. Its role in the initial stages of apoptosis is summarized above. Once the apoptotic cell has reached the terminal stages of apoptosis (i.e., loss of membrane integrity), it will be appreciated that the PS in both plasma membrane leaflets will be "exposed" to the extracellular milieu. A similar situation exists in cell death by necrosis, where the loss of membrane integrity is either the initiating factor or occurs early in the necrotic cell death process; accordingly, such necrotic cells also have "exposed" PS, since both plasma membrane leaflets are "exposed".

IV. Annexin

The annexin family of proteins is useful in the practice of the present invention. Annexin V is normally found in high levels in the cytoplasm of a number of cells including placenta, lymphocytes, monocytes, biliary and renal (cortical) tubular epithelium. Although the physiological function of annexins has not been fully elucidated, several properties of annexins make them useful as diagnostic and/or therapeutic agents. In particular, it has been discovered that annexins possess a very high affinity for anionic phospholipid surfaces, such as a membrane leaflet having an exposed surface of phosphatidylserine (PS).

V. Overview of Experimental Results

Experiments performed in support of the present invention have demonstrated that administration of radiolabeled annexin can be used to image cell death in vivo. For instance, experiments in Example 1 describe the imaging and quantification of Fas-mediated hepatocyte death in response to injection of purified Jo2 antibody in mice (Ogasawara, et al., 1993). Results of these experiments (see, e.g. FIG. 1) showed a two- and four-fold increase in hepatic uptake of radiolabeled annexin V at one and two hours, respectively, specifically due to Fas-mediated hepatocyte death following Jo2 antibody injection. A transient two-fold increase in splenic uptake early after treatment, which subsequently fell to control values, was also observed. This decline in signal from spleen may have been due to a rapid clearance of circulating and splenic lymphocytes in response to a burst of Fas-mediated apoptosis following treatment.

Annexin binding was also observed in the kidneys. However, this binding was present in the absence of any apoptosis-inducing stimulus, and in fact, decreased as the hepatocyte signal increased. The progressive reduction in the renal activity with time following anti-Fas Ab administration, together with increasing hepatic uptake in the same period, implies that the non-apoptotic-related renal affinity for annexin V is lower than that of apoptotic tissue. Renal cortical binding of injected annexin V may be in part due to annexin's cross reactivity with renal tubular phospholipid.

It will be noted that there was little renal excretion of labelled annexin, suggesting that the radiolabel (in this case, Tc99m), remained linked to the annexin for the duration of the experiments. Further, injected Tc99m-labeled annexin was rapidly cleared from the bloodstream, having a serum half-life of about 3-7 minutes. These factors allowed for imaging of the radiopharmaceutical signal 1 to 2 hours after its administration.

The above-described characteristics enable serial daily (or bi-daily) imaging studies each of which represent snapshot of apoptotic activity with a tissue or organ of interest at the time of injection of the radiolabeled annexin V.

VI. Imaging Cell Death In Vivo

The present invention includes, in one aspect, a method of imaging cell death (due, e.g., to apoptosis or necrosis) in a region of a mammalian subject in vivo. In the method, a radiolabeled annexin (e.g., technetium 99m-labeled annexin V) is administered to the subject. After a period of time in which the conjugate can achieve localization in the subject, the subject is placed within the detection field of a gamma ray detector device. The subject is maintained in a substantially immobilized condition while gamma ray emission from the technetium 99m is measured using the gamma ray detector device. Following the measuring phase, an image of gamma ray emission is constructed. The image so constructed is then used to provide the attending clinician with a map or a localization of areas of cell death in the mammalian subject, or in the region of the mammalian subject that is being analyzed.

To facilitate interpretation of an image obtained using the above method, the image may be digitally processed to filter out background, noise and/or non-specific localization (e.g., kidney localization) of the annexin/Tc99m conjugate, as described in more detail below.

An advantage of the above method is that, by measuring the gamma ray emission and forming an image at selected intervals, the method can be used to track changes in the intensity of gamma ray emission from the subject over time, reflecting changes in the number of cells undergoing cell death. Such an approach may also be used to track changes in the localization of gamma ray emission from the subject over tune, reflecting changes in the distribution of cells undergoing cell death.

A. Synthesis of Radiolabeled Annexin

The invention can be practiced using purified native, recombinant, or synthetically-prepared annexin. Annexin V, for example, may be conveniently purified from human placenta (Funakoshi, et al., 1987). Recombinant annexin offers several advantages, however, including ease of preparation and economic efficiency. A number of different annexins have been cloned from humans and other organisms. Their sequences are available in sequence databases, including GenBank.

The invention is preferably practiced using annexin V, for several reasons. First, annexin V is one of the most abundant annexins, (ii) it is simple to produce from natural or recombinant sources, and (iii) it has a high affinity for phospholipid membranes (Tait, et al., 1988). Human annexin V has a molecular weight of 36 kd and high affinity (kd 7 nmol/L) for phosphatidylserine (PS). The sequence of human annexin V can be obtained from GenBank under accession numbers U05760-U05770.

An exemplary expression system suitable for making annexin for use with the present invention is referred to in the Materials and Methods. It employs the pET12a expression vector (Novagen, Madison, Wis.) in *E. coli*.

Other bacterial expression vectors can be utilized as well. They include, e.g., the plasmid pGEX (Smith, et al., 1988) and its derivatives (e.g., the pGEX series from Pharmacia Biotech, Piscataway, N.J.). These vectors express the polypeptide sequences of a cloned insert fused in-frame with glutathione-S-transferase. Recombinant pGEX plasmids can be transformed into appropriate strains of *E. coli* and fusion protein production can be induced by me addition of IPTG (isopropyl-thio galactopyranoside). Solubilized recombinant fusion protein can then be purified from cell lysates of the induced cultures using glutathione agarose affinity chromatography according to standard methods (Ausubel, et al). Other commercially-available expression systems include yeast expression systems, such as the *Pichia* expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ion-exchange chromatography, isoelectric focusing, gel electrophoresis and affinity chromatography. Protein preparations can also be concentrated by, for example, filtration (Amicon, Danvers, Mass.).

Annexin produced as described above is then labeled with a selected radionuclide. The particular isotope selected will depend on the particular application of the claimed method.

The invention may be practiced with any one of a variety of radionuclides presently available. In selecting a suitable radionuclide, the practitioner will typically consider the particular application of the invention, along with factors common to nuclear imaging in general. Such factors include (i) minimum of particle emission, (ii) primary photon energy of between about 50 and 500 kEv, (iii) physical half-life greater that the time required to prepare material for administration, (iv) effective half life longer than the examination time, suitable chemical form and reactivity, low toxicity, and stability or near stability of annexin labeled with that radionuclide.

An exemplary radionuclide is Tc99m, which has a half-life of about 6 hours and can be used to label annexin to high specific activities. It fulfills most of the above criteria and is used in over 80% of nuclear medicine imaging procedures. Other isotopes which may be used include Iodine 123 (half-life of ~13.2 hours), Iodine 131 (half-life of ~8 days), Gallium 67 (half-life of ~78 hours), and Indium 111 (half-life of ~2.8 days).

Linking of the isotope to annexin can be accomplished using known techniques. For example, Tc99m can be linked to annexin through the use of a hydrazino nicotinamide (HYNIC) group, available, e.g., from AnorMED, Langley, British Columbia, Canada, as described below in the Materials and Methods section. Gallium 67 and Indium 111 can be used to radiolabel proteins using, for example, the method described by Hnatowich, et al., 1983, incorporated herein by reference.

Other methods for labeling proteins with radionuclides are known. For example, U.S. Pat. No. 5,552,525, issued Sep. 3, 1996 (Dean), teaches the making of technetium-99m (Tc-99m) labeled peptides. Methods for labeling peptides and polypeptides with Tc-99m are also disclosed in U.S. Pat. Nos. 5,443,815 and 5,508,020. Lind, et al., (1990) teach Tc-99m labeled monoclonal antibodies. LaMuraglia, et al., (1989) teach $^{111}$In-labeled non-specific human immunoglobulin, and Fischman, et al., (1991) teach chemotactic formyl peptide (fMLF)—$^{111}$In-labeled DTPA conjugates.

B. Administration of Radiolabeled Annexin

Radiolabeled annexin may be administered using standard protocols for administration of radiolabeled compounds. The dosage depends on two primary considerations: (i) the amount and type of radionuclide injected, and (ii) the amount of annexin protein injected.

Technetium 99m can be administered to adult humans at doses up to about 20 mCi. The preferred dose for a single Tc99m administration is between about 5 and 20 mCi.

Annexin V begins to have pharmacological effects (anti-coagulant effects) at doses greater than about 300 μg/kg. Accordingly, the diagnostic methods of the present invention (which seek to avoid pharmacological effects of the labeled annexin) are preferably practiced at doses lower than 300 μg/kg, typically less than about 50 μg/kg. Such tracer doses (e.g., 10 μg/kg to 50 μg/kg) have no reported pharmacologic or toxic side effects in animal or human subjects.

The radiolabeled annexin is typically suspended in a suitable delivery vehicle, such as sterile saline. The vehicle may also contain stabilizing agents, carriers, excipients, stabilizers, emulsifiers, and the like, as is recognized in the art.

Radiolabeled annexin can be administered by any of several routes known to be effective for administration of radiolabeled proteins for nuclear medicine imaging. A preferred method of administration is intravenous (i.v.) injection. It is particularly suitable for imaging of well-vascularized internal organs, such as the heart, liver, spleen, etc. Methods for i.v. injection of radiopharmaceuticals are known. For example, it is recognized that a radiolabeled pharmaceutical is typically administered as a bolus injection using either the Oldendorf/Tourniquet method or the intravenous push method (see, e.g., Mettler and Guierbteau, 1985, Appendix D).

For imaging the brain, the labeled annexin can be administered intrathecally. Intrathecal administration delivers compound directly to the sub-arachnoid space containing cerebral spinal fluid (CSF). Delivery to spinal cord regions can also be accomplished by epidural injection to a region of the spinal cord exterior to the arachnoid membrane.

Other modes of administration include intraperitoneal (e.g., for patients on kidney dialysis), and intrapleural administration. For specific applications, the invention contemplates additional modes of delivery, including intramuscular injection, subcutaneous, intralymphatic, insufflation, and oral, intravaginal and/or rectal administration.

Methods for practicing the modes of administration listed above are known in the art.

C. Localization of Radiolabeled Annexin

After the labeled annexin is administered, it is allowed to localize to the target tissue or organ. Localization in this context refers to a condition when either an equilibrium or a pseudo-steady state relationship between bound, "localized", and unbound, "free" labeled annexin within a subject has been achieved. The amount of tune required for such localization is typically on the order of minutes to tens of minutes. It can be estimated by the serum half-life of the labeled annexin. In the case of Tc99m-labeled annexin V injected i.v., the serum half life is between about 3 and 7 minutes. The localization tune also depends on the accessibility of the target tissue to the labeled annexin. This in turn depends on the mode of administration, as is recognized in the art.

Imaging is preferably initiated after most of the labeled annexin has localized to its target(s). For i.v. administered Tc99m-labeled annexin V, this occurs after several half-lives. A duration of about 10 half-lives (about 30-70 min in the case of annexin/Tc99m conjugates) is considered to be ample tune to achieve essentially complete localization. One of skill in the art will appreciate, however, that it may be desirable to perform the imaging at times less than or greater than the ~10 half-life timepoint described above. For example, in imaging cell death due to blood vessel injury, the accessibility of the target tissue is very high, such that a strong signal can be obtained from the target site in only a few minutes, especially if a low dose of labeled annexin is administered gradually to minimize signal from circulating label.

In all of the above cases, a reasonable estimate of the time to achieve localization may be made by one skilled in the art. Furthermore, the state of localization as a function of time may be followed by imaging the gamma ray signal from the labeled annexin according to the methods of the invention.

D. Gamma Ray Detection Devices

Gamma ray imaging devices function by accumulating signal arising from gamma rays emitted from the subject over time. One of the most widely-used methods for gamma ray detection is the Anger gamma scintillation camera (Mettler and Guiberteau, 1985). It operates by converting gamma rays emitted by the radionuclide into photons (usually with NaI(Tl) crystals), which are then amplified in photomultiplier tubes (PMTs), converted to a voltage signal, and used to construct an image. The components of an Anger scintillation camera typically include a collimator, a scintillation crystal, an array of PMTs, a pulse height analyzer, a cathode ray tube (CRT), and a control console. The camera system also typically includes a computer. The processing between the PMTs and the display (e.g., CRT) can be either analog or digital. A detailed description of the theory and operation of Anger gamma scintillation cameras can be found in any of a number of reviews and/or nuclear medicine texts (see, e.g., Mettler and Guiberteau, 1985, incorporated herein by reference).

A more informative image may be obtained using emission-computed tomography (ECT) to generate a 3-dimensional image. The two primary types of ECT are single photon emission computed tomography (SPECT), which uses isotopes such as Tc-99m, and positron-emission tomography (PET), which relies on high-energy (511-keV) annihilation photons to provide highly accurate localization. A disadvantage of PET is that it is typically used with short-lived cyclotron-produced isotopes, like $^{11}$C, is $^{13}$N, and $^{18}$F. SPECT, on the other hand, can be used with the types of radiopharmaceuticals described herein (e.g., Tc-99m).

SPECT systems typically include one or two computer-controlled Anger gamma scintillation camera heads that can rotate about the patient in a circular or elliptical orbit. Such SPECT cameras are available from a number of suppliers. For example, Siemens (Des Plains, Ill.) sells several such cameras, including the "E-CAM", "ORBITER", "ECAT", "MULTISPECT 3", "MULTISPECT 2" and the "DIACAM".

Cameras such as described above now typically include integrated image processors which can manipulate images as digital files to subtract background, add pseudo-color and the like. Once the images are in the form of digital files, they can be manipulated by a variety of image processing programs (e.g., "ADOBE PHOTOSHOP", Adobe Systems, Adobe Systems, Mt. View, Calif.) on a personal computer, such as an IBM-compatible PC or an Apple Macintosh (Apple Computer, Cupertino, Calif.) and printed.

E. Placing Subject in the Field of a Gamma Ray Detection Device

1. Detection Field of Device. The detection field of the device is defined as the area from which consistent and reliable measurements of gamma ray emission can be obtained. If ECT is being used to generate the image, the detection of the device is the entire space from which gamma ray emission can be reliably measured, or the portion of such space that the ECT system is programmed to include in the scan. This space is typically substantial larger than the detection field of a single, non-ECT camera.

It will be understood that the entire animal or subject need not necessarily be in the detection field of the gamma ray detection device. For example, if one is interested in analyzing the signal from a particular organ, only signal from the region containing the organ, and a sufficient surrounding "dark" zone, need be measured to obtain the desired information.

2. Placing the Subject: Immobilization. To collect the signal which is used to generate an image, the subject is located in the detection field of the photodetection devices during the period that gamma rays which will be used to construct an image are being measured. If the signal is sufficiently strong that an image can be constructed from gamma ray emission measured in less than about 20 milliseconds, and/or the subject does not move relative to the imaging plane sufficiently to substantially deteriorate the image, no special immobilization precautions are typically required. All that is required is that the subject be located in the field of the detection device for the extent of the measuring period.

If, on the other hand, the gamma ray emission measurement takes longer than about 20 msec, and the subject is agitated, precautions to insure immobilization of the subject during gamma ray emission measurement, commensurate with the degree of agitation of the subject, should be considered to preserve the spatial information in the constructed image. For example, in a case where the subject is a person and photon emission measurement time is on the order of a few seconds, the subject may simply be asked to remain as still as possible during gamma ray emission measurement (imaging). On the other hand, if the subject is an animal, such as a mouse, the subject can be immobilized using, for example, an anesthetic or a mechanical restraining device.

A variety of restraining devices may be constructed. For example, a restraining device effective to immobilize a mouse for tens of seconds to minutes may be built by fastening a sheet transparent to gamma rays over a foam cushion. The cushion has an indentation for the animal's head at one end. The animal is placed under the sheet such that its head is over the indentation, allowing it to breathe freely, yet the movement of its body is constrained by the foam cushion.

It will be understood that the region imaged may include substantially the entire subject, or only a part of the subject which needs to be diagnosed or monitored for cell death. For example, the region may include only an appendage or part of such appendage, the head, the central nervous system or an internal cavity, such as (he thoracic or peritoneal cavity. In specific embodiments, the regions may contain only a selected organ or portion thereof. For example, the method may be applied to analysis of cell death only in the central nervous system, brain, heart, liver, spleen, lungs, bone marrow, or a portion of any of the above. Further, the region analyzed may be restricted to a tumor, e.g., in a cancer patient undergoing treatment designed to cause cell death in the tumor.

F. Constructing an Image of Gamma Ray Emission: Image Processing

In most suitable cameras, the measurement of gamma ray emission generates a voltage signal which can either be displayed on a CRT or stored and/or analyzed by a computer as an array of numbers. These numbers are used to generate an image by standard imaging methods. For example, the image is typically analyzed by normalizing the gamma ray counts (either to a fixed, pre-selected value, or to the maximum number detected in any pixel) and converting the normalized number to a brightness (greyscale) or to a color (pseudocolor) that is displayed on a monitor. In a pseudo-color representation, typical color assignments are as follows. Pixels with zero counts are assigned black, low counts blue, and increasing counts colors of increasing wavelength, on up to red for the highest gamma ray count values. The location of colors on the monitor represents the distribution of gamma ray emission, and, accordingly, the location of areas of cell death.

If it is desired to follow the localization and/or the signal over tune, for example, to record the effects of a treatment on the distribution and/or localization of cell death, the measurement of gamma ray emission, or imaging can be repeated at selected time intervals to construct a series of images. The intervals can be as short as minutes, or as long as days, weeks, months or years.

Images generated by methods of the present invention may be analyzed by a variety of methods. They range from a simple visual examination, mental evaluation and/or printing of a hardcopy, to sophisticated digital image analysis.

VII. Applications

Major uses for radiolabeled annexin V include the detection of inappropriate apoptosis in disease states where it should not occur, e.g., immune disorders such as Lupus, transplant rejection, or in cells subject to severe ischemia; and the detection of insufficient apoptosis when it should occur, e.g., tumors or cells infected with virus.

The results described herein indicate that radiolabeled annexin can be employed in a variety of clinical settings in which apoptotic and/or necrotic cell death need to be monitored, such as, without limitation, organ and bone marrow transplant rejection or injury, infectious and non-infectious inflammatory diseases, autoimmune disease, cerebral and myocardial infarction and ischemia, cardiomyopathies, atherosclerative disease, neural and neuromuscular degenerative diseases, sickle cell disease, β-thalassemia, cancer therapy, AIDS, myelodysplastic syndromes, and toxin-induced liver disease, etc. Radiolabeled annexin may also be useful as a clinical research tool to study the normal immune system, embryological development, and immune tolerance and allergy.

Radiolabeled annexin V can be used, for example, to image and quantify apoptotic cell death in normal and malignant tissues undergoing treatment. Monitoring apoptosis with serial imaging studies using radiolabeled annexin V can be used for the rapid testing and development of new drugs and therapies in a variety of diseases. In addition, the methods may be used to monitor the progress of treatment, monitor the progress of disease, or both. Further, they may be used to aid in early detection of certain diseases.

The following examples illustrate but in no way are intended to limit the present invention.

MATERIALS AND METHODS

A. Preparation of HYNIC Labeled Annexin V

Human annexin V was produced by expression in E. coli from the pET12a-PAPI plasmid and purified as previously described (Wood, et al., 1996, incorporated herein by reference). A 30 mM stock solution ("HYNIC ester stock") of the N-hydroxysuccinimide ester of hydrazino nicotinamide (HYNIC; obtained from AnorMED, Langley, British Columbia, Canada; Babich et al., 1993, incorporated herein by reference) was prepared by suspending 220/µg of succinimidyl 6-hydrazinonicotinate hydrochloride (SHNH) in 18.5 µL of N,N-dimethyl formamide. Five mg of annexin V dissolved to 893 µL of Buffer A (20 mM HEPES, pH 7.4, 100 mM NaCl) were reacted with the HYNIC ester stock for three hours with gentle stirring shielded from light at room temperature according to the method described by Schwartz, et al., 1991, incorporated herein by reference. The reaction was quenched with 500 µL of 500 mM glycine pH 5.3 then dialyzed at 4° C. against 20 mM sodium citrate, pH 5.2, 100 mM NaCl. Precipitate was removed by centrifugation at 1500×g for ten minutes. 100 µL (100 µg) aliquots of HYNIC-annexin V were stored at −70° C.

B. Radiolabeling of HYNIC-Annexin V

80 µL of $SnCl_2$ (50 mg/ml in 0.1 N HCl purged for two hours with $N_2$ gas) was added to 50 ml of a 20 mM tricine solution (pH 7.1, purged for one hour with $N_2$ gas; tricine=N-[tris (hydroxymethyl)methyl] glycine). 200 µL of the Sn-tricine solution was added to 100 µL of Tc99m (4-8 mCi activity) mixed with a 100 µL aliquot of annexin V (prepared as described above) according to the methods described by Larson, et al., 1995.

Specific activity of radiolabeled annexin was 20-200 µCi/µg protein (depending on desired activity) with radiopurity of 92%-97% determined with instant thin layer chromatography ITLC) using saline as the solvent. Membrane binding activity of HYNIC-annexin V and decayed Tc99m HYNIC annexin V was determined by a modified competition assay in which 5 nM FITC-annexin V was substituted for $I^{125}$ annexin V (Wood, et al., 1996). After 15 minutes at room temperature, the sample was centrifuged, the FITC-annexm V bound to the pelleted cells was released with EDTA and the released FITC-annexm V measured by fluorometry. In this assay system, unmodified annexin, HYNIC annexin, and Tc99m HYNIC annexin V had competitor inhibiting (50% concentrations of the binding of FITC-annexin V) of 8 nM, 10.5 nM, and 12.3 nM, respectively. Incorporation of HYNIC into annexin V was found to be 0.9 mol per mole of annexin V.

C. Imaging and Biodistribution Studies

Mice were injected with 50-150 µCi of Tc99m-HYNIC annexin (0.125-0.25 µg of protein) after determination of free versus bound Tc99m using ITLC saline as a solvent. Mice were imaged one to two hours after injection of radiopharmaceutical in the prone position. Images were acquired for 15 minutes using a Low Energy Mobile (LEM) scintillation camera with a high sensitivity parallel hole collimator and a 128×128 imaging matrix (Siemens, Des Plains, Ill.). The same protocols were used for all scans pre- and post-treatment.

Biodistribution studies were performed after harvesting specimens of cervical nodes/salivary glands, brain, thymus, heart, lungs, liver, spleen, stomach, GI tract, kidneys, skeletal muscle, fat, blood, and remaining carcass. Samples were counted on a Packard Cobra n autogamma scintillation counter (Packard Instrument, Downers Grove, Ill.) expressed as corrected counts per minute for isotope decay and background activity.

D. Lnmunostaining for Bound Human Annexin V and Apoptotic Nuclei

Formalin-fixed paraffin-embedded tissues were sectioned at 5 µm for staining with hematoxylin/eosin or other techniques. Immunostaining for bound human annexin V was performed with a rabbit anti-serum raised against human placental annexin V and affinity purified with recombinant annexin V coupled to Affi-Gel (Bio-Rad). Immunohistochemical detection then was completed by sequential incubations with biotin-labeled goat anti-rabbit antibody and avidin-horseradish peroxidase complex (Jackson Immuno Research), followed by reaction with 3,3'-diaminobenzidine as described by Bindl and Wamnke (Bindl, J. M. & Warnke, R. A., 1986, incorporated herein by reference).

For the detection of apoptotic nuclei, sections were stained using a modification of the terminal deoxynuclectidyltransferase-mediated UTP end labeling (TUNEL) method described by Gavrieli et al. (Gavrieli, et al., 1992, incorporated herein by reference). After inhibition of endogenous peroxidase, deparaffinized sections were digested with proteinase K (20 µg/ml) for 15 min at room temperature. Sections were then incubated with λ exonuclease (Life Technologies, Gaithersburg, Md.) at 5 unit/ml for 30 min at 37° C. followed by equilibration with terminal deoxynucleotidyltransferase reaction buffer (0.2 M potassium cacodylate, 25 mM Tris-HCL, 0.25 mg/ml BSA, 1.5 mM $CaCl_2$, 20 mg/ml polyvinylpyrrolidone, and 20 mg/ml Ficoll) and 5 µM dATP. The end-labeling reaction then was performed in terminal deoxynucleotidyltransferase reaction buffer also containing a final concentration of 75 unit/ml of terminal deoxynucleotidyltransferase and 100 µM of 1,N-6-ethenol-dATP (Sigma). After a 60-min incubation at 37° C., the reaction was quenched via rinsing with 1×SSC (standard saline citrate). Sections were then incubated with murine 1G4 mAb (gift from Regina Santella, Columbia University), which recognizes the ethenoadenine moiety (Young, T. L. & Santella, R. M., 1988, incorporated herein by reference). Subsequent immunohistochemical detection was as described above, using a biotin-labeled goat anti-mouse antibody.

EXAMPLE 1

In Vivo Imaging of Fas-Mediated Apoptosis

Liver apoptosis in mice was induced by injection of anti-Fas antibody, which causes extensive liver apoptosis within one to two hours followed by death at three hours in 90% of treated animals (Ogasawara).

Five to six week old 18-24 gram female Balb/c mice were injected intravenously (i.v.) with purified hamster monoclonal anti-Fas antibody (Jo2, 10 µg per animal, Pharmingen, San Diego, Calif.). Following injection with the anti-Fas antibody, the animals were injected intravenously with about 90 µCi of technetium 99 m (Tc99m) hydrazino nicotinamide (HYNIC) radiolabeled annexin V at 0, 1, and 2 hours following antibody administration in three separate experiments. The results are shown in FIG. 1.

A marked progressive increase in hepatic uptake of radiolabeled annexin V was observed at one and two hours, corresponding to 148% and 372% of control values, respectively, as determined by the region-of-interest (ROI) image analysis illustrated in FIG. 1. Splenic uptake transiently rose to 140% of control values at one hour following treatment falling to 110% at two hours. Renal uptake fell 40% at one and two hours after treatment.

Figure 2:
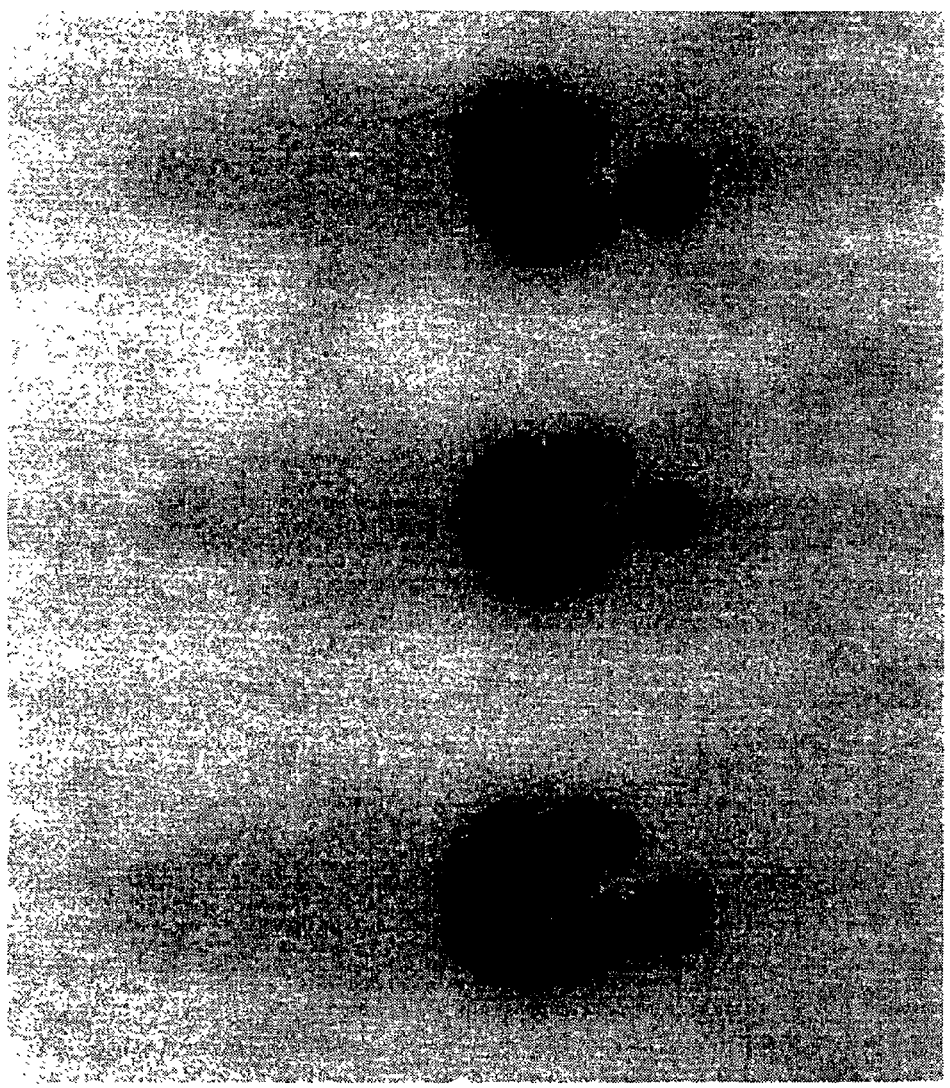
FIG. 2 is a computer-generated image showing signal from Tc99m HYNIC-ovalbumin during Fas-mediated fulminant hepatic apoptosis.

Another group of mice (control) were injected with 90 µCi of Tc99m HYNIC ovalbumin (MW=43 kd; 2 µg of protein) at 0, 1, and 2 hours after Jo2 antibody treatment. As shown in FIG. 2, these animals demonstrated an initial increase in hepatic uptake a one hour (127%) which remained unchanged at two hours (131%) after anti-Fas antibody treatment. Splenic uptake of radiolabeled ovalbumin remained unchanged from control values after treatment. Renal uptake of radiolabeled ovalbumin increased 138% at one hour and plateaued at 131% of control values at two hours following treatment.

A third group of mice were treated as above and co-injected with Tc99m labeled annexin V and $I^{125}$ labeled human serum albumin (HSA) at 0,1 and 2 hours in three separate experiments. The annuals in the different experiments were sacrificed after each corresponding timepoint and underwent biodistribution study. The results, expressed as percent injected dose per gram of tissue (% ID/gm), are shown in Table 1, below. The data were proportional to those obtained by ROI image analysis for both radiolabeled annexin V and HSA.

TABLE 1

Biodistribution Assay of Radiolabeled Annexin V and HSA

| Tc99m Annexin V | Controls | Anti-Fas Treated Mice (10 µg/mouse) | |
|---|---|---|---|
| % I.D./gm | (N = 6) | 1 hr. (N = 8) | 2 hr. (N = 6) |
| Liver | 11.7 ± 1.35 | 15.0 ± 3.5* | 41.6 ± 10.0** |
| Kidney | 187.9 ± 21.8 | 127.7 ± 42.6* | 64.9 ± 37.5** |
| Spleen | 12.1 ± 1.08 | 20.8 ± 7.8* | 17.5 ± 7.55 (N.S.) |
| $I^{125}$HAS | Controls | Anti-Fas Treated Mice (10 µg/mouse) | |
| % I.D./gm | (N = 4) | 1 hr. (N = 6) | 2 hr. (N = 5) |
| Liver | 3.87 ± 0.76 | 6.92 ± 1.81* | 6.87 ± 1.2** |
| Kidney | 4.6 ± 0.89 | 6.0 ± 0.42* | 5.84 ± 0.88** |
| Spleen | 3.2 ± 0.67 | 3.75 ± 0.86 (N.S.) | 3.42 ± 0.56 (N.S.) |
| Organ Weight | Controls | Anti-Fas Treated Mice | |
| (grams) | (N = 6) | 1 hr. (N = 8) | 2 hr. (N = 6 |
| Liver | 1.02 ± 0.086 | 1.41 ± 0.37** | 1.32 ± 0.25* |
| Kidney | 0.33 ± 0.061 | 0.34 ± 0.082 (N.S.) | 0.34 ± 0.048 (N.S.) |
| Spleen | 0.11 ± 0.023 | 0.12 ± 0.02 (N.S.) | 0.11 ± 0.018 (N.S.) |
| TOTAL BODY | 19.5 ± 1.1 | 20.7 ± 2.2 (N.S.) | 19.3 ± 1.6 (N.S.) |

*Significantly (p, 0.05) different from control values.
**Highly significant (p, 0.001) different from control values.
N.S. Not significantly different from control values.
N.B. statistical comparisons of average values were performed with a two-tailed Student's T-test.

EXAMPLE 2

In Vivo Imaging of Cardiac Alloeraft Rejection $^{99m}$Tc HYNIC-annexin V was prepared substantially as described above. Imaging and biodistribution studies were conducted as above, except where specified otherwise.

Adult male ACI rats (250-350 g) received heterotopic cardiac allografts from PVG donors (obtained from Harlan-Sprague-Dawley) anastomosed to the hosts' abdominal aorta and inferior vena cava according to a modification of the technique of Ono and Lindsey (Woodley, et. al., 1993, incorporated herein by reference). Syngeneic cardiac isografts from ACI donors also were transplanted to the abdomens of host ACI rats. PVG cardiac allografts in ACI recipients using the model above begin to undergo rejection between 4 and 5 days post-transplantation as assessed by decreased pulsation to palpitation. Five days after transplantation all of the animals received 700-900 µCi of $^{99m}$Tc HYNIC-annexin V (10-20 µg protein/kg) via tail vein and were imaged 1 hour later. Animals were then sacrificed, and native and transplanted hearts underwent scintillation counting and hisopathologic studies.

All of the PVG cardiac allografts (n=4) were visualized easily with $^{99m}$Tc HYNIC-annexin V 5 days after transplantation. ACI syngeneic cardiac isografts (n=3) had no visible activity after injection of $^{99m}$ Tc HYNIC-annexin with uptakes of radiopharmaceutical identical to native cardiac activity as confirmed by scintillation well counting. The percentage of whole body activity of PVG allografts was 213% above ACI isograft activity (P<0.005; using a two-tailed student's t test) determined by ROI image analysis. Scintillation well-counting assay revealed a greater than 11-fold increase in $^{99m}$ Tc HYNIC-annexin V uptake in PVG allografts as compared with native heart activity. Sections of PVG cardiac allografts 5 days after transplantation showed a marked mononuclear inflammatory cell infiltrate in all animals; no infiltrate was observed in syngeneic or native hearts. The infiltrate surrounded areas of myocardial injury and was associated with thrombosis of myocardial vessels. In the center of these areas, there was frank necrosis, with no staining by hematoxylin, but at the periphery, there were nuclei with changes of apoptosis as confirmed by TUNEL staining. Immunostaining for $^{99m}$Tc HYNIC-annexin "V was observed in a granular pattern in cardiac myocytes at the junction of inflamed and necrotic areas; the nuclei of these cells were stained still by hematoxylin, further suggesting that they were apoptotic rather than necrotic. Anti-annexin V staining was far more extensive in terms of the number of positive myocytes and intensity compared with TUNEL. Anti-annexin staining was heavy and clumped in frankly necrotic areas as expected but was specific; no staining was observed in syngeneic or native hearts or in staining of allografted hearts in which the primary antibody was omitted.

In a separate, but similar, set of experiments, ACI rats (n=6 in each group) received heterotopic cardiac allografts from PVG donors. Syngeneic cardiac isografts from ACI donors (n=3 in each group) were transplanted to host ACI rats. Neither group received treatment for transplant rejection.

Groups of recipient rats underwent nuclear scanning at day 1, 2, 3, 4, 5, 6, and day 7 post-transplantation. 1.0 mCi $^{99m}$Tc HYNIC-annexin V was injected 1 hour prior to nuclear scanning.

The PVG cardiac allografts were visualized easily with $^{99m}$Tc HYNIC-annexin V 4 days after transplantation. ACI syngeneic cardiac isografts had no visible activity after injection of $^{99m}$Tc HYNIC-annexin.

Figure 3:
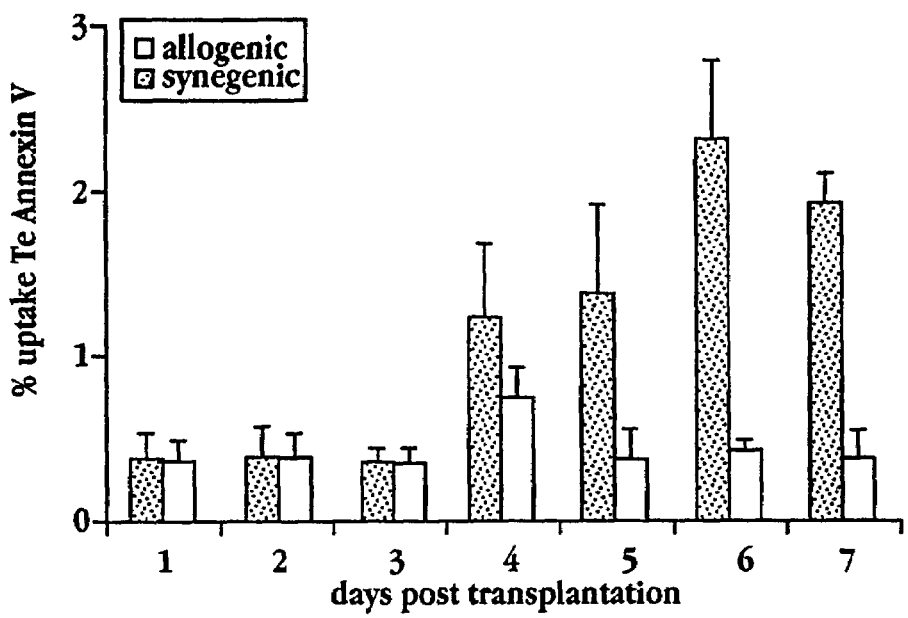
FIG. 3 is a graph depicting the percent uptake of 99mTc HYNIC-annexin V for days 1-7 post transplantation of syngenic or allogenic cardiac isografts in ACI rats.

Region of interest analysis jvas vised to quantify uptake of $^{99m}$Tc HYNIC-annexin V. Uptake by the transplanted heart was calculated as percentage of total body uptake. The results are depicted in FIG. 3.

Immediately after nuclear scanning, animals were euthanized. Transplanted hearts were harvested for analysis. Histologic grading of acute rejection was performed on standard hematoxylin and eosin stained sections. The grading scheme is shown in Table 2, below.

TABLE 2

Histologic Grading of Acute Rejection

| | |
|---|---|
| Grade 0 | No Rejection |
| Grade 1 | Mild Rejection |
| Grade 2 | Moderate Rejection |
| Grade 3 | Severe Rejection |

Apoptotic nuclei were identified in histologic sections by TUNEL staining of nuclear DNA cleavage, using a commercially available peroxidase kit (APOPTAG®, Oncor, Gaithersburg, Md.). As indicated by the data of Table 3, apoptosis appears to occur in myocytes and inflammatory cells during cardiac allograft rejection.

TABLE 3

TUNEL Staining in Cardiac Allografts;
Presence of Positive Nuclei during Rejection

| Rejection | Inflammatory Cells | Endothelial Cells | Myocytes |
|---|---|---|---|
| Grade 0 | 0 | 0 | 0 |
| Grade 1 | + | + | + |
| Grade 2 | ++ | + | + |
| Grade 3 | + | + | ++ |

Figure 4:
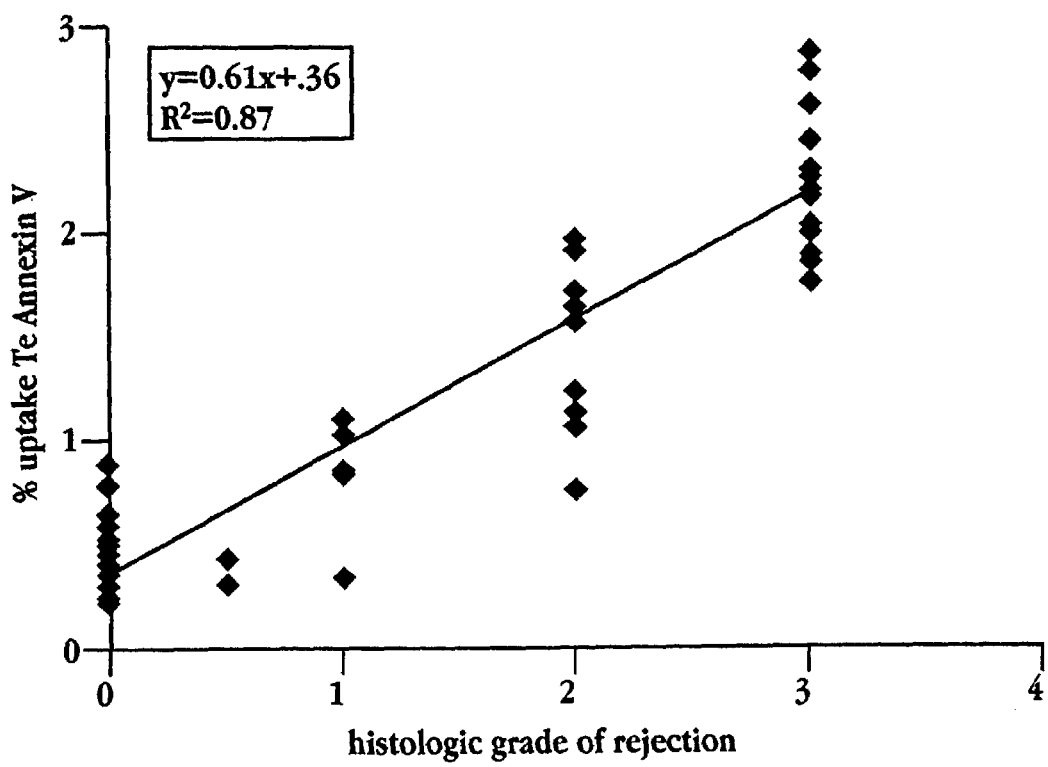
FIG. 4 is a graph depicting the percent updake of 99 mTc HYNIC-annexin V during cardiac allograft rejection in ACI rats.

As shown by the data of Table 4, below, and the graph of FIG. 4, the uptake of $^{99m}$Tc HYNIC-annexin V correlates with histologic grades of acute rejection.

TABLE 4

Percent Uptake of $^{99m}$Tc HYNIC-annexin V
during Cardiac Allograft Rejection

| Rejection | % Uptake ± stdv | Significance* |
|---|---|---|
| Grade 0 | 0.42 ± 0.17 | |
| Grade 1 | 0.83 ± 0.31 | P = 0.036 vs. Grade 0 |
| Grade 2 | 1.43 ± 0.40 | P = 0.008 vs. Grade 1 |
| Grade 3 | 2.40 ± 0.53 | P = 0.001 vs. Grade 2 |

*Student's t-test, two tailed, unequal variance

EXAMPLE 3

In Vivo Imaging of Treated Murine Lymphoma $^{99m}$Tc HYNIC-annexin V was prepared substantially as described above. Imaging and biodistribution studies were conducted as above, except where specified otherwise.

38C13 murine B cell lymphomas (Maloney, et al., 1985) were grown to C3H.HeN mice (Harlan Breeders, Indianapolis) following s.c. injection of 400 tumor cells suspended in 200 μl of RPMI medium 1640 (without serum) into the left flank. Fourteen days after implantation mice underwent treatment with 100 mg/kg of cyclophosphamide injected i.p. Mice were injected i.v. with 25-50 μg/kg of $^{99m}$Tc HYNIC-annexin V (100-150 μCi/animal) 20 hours after cyclophosphamide administration. Animals were then imaged and sacrificed 1 hr after injection of radiopharmaceutical after tumor removal for scintillation counting and histopathologic studies.

Untreated flank tumor implants (n=8) were seen easily by scintillation camera imaging and had an annexin V uptake 365% above normal soft tissue activity as shown by ROI image analysis. Treated flank tumors (n=6) showed readily visualizable increases in $^{99m}$TcHYNIC-annexin V activity of 78% above control values expressed as whole body activity per gram of tumor (P<0.05 using a two-tailed student's t test for significance). This result was confirmed by scintillation well counting in which treated tumors demonstrated a 132% increase in annexin V uptake expressed as percentage of injected dose per gram of tumor (P<0.05) with a 58% fall in weight (P<0.05) compared with the control. The whole body activity per gram of tumor as seen by ROI image analysis linearly correlated to percentage of injected dose per gram of tumor determined on biodistribution study ($r^2$=0.831). Histologic analysis demonstrated virtually complete (greater than 95%) apoptosis of all lymphoblasts in treated tumors with less than 5% apoptotic cells in controls.

While the invention has been described with reference to specific methods and embodiments, it is appreciated that various modifications and changes may be made without departing from the invention.

The invention claimed is:

1. A method of imaging phosphatidylserine exposure on a nucleated cell within a region of a human subject in vivo, comprising
    (a) administering to the human subject, annexin labeled with a biocompatible radionuclide,
    (b) positioning the human subject within the detection field of a radiation detector device, and
    (c) measuring radiation emission from the radionuclide localized in the human subject, with the radiation detector device, to construct an image of radiation emission,
    wherein said image is a representation of phosphatidylserine exposure on said nucleated cell within a region of said human subject.

2. The method of claim 1, wherein the radionuclide is selected from the group consisting of Iodine 123, Iodine 131, Gallium 67, Indium 111, Fluorine 18, and Technetium 99 m (Tc99m).

3. The method of claim 2, wherein the radionuclide is technetium 99 m (Tc99m).

4. The method of claim 3, wherein the Tc99m is linked to the annexin via hydrazino nicotinamide (HYNIC).

5. The method of claim 3, wherein the amount of Tc99m-labeled annexin administered results in a dose of between about 5 mCi and about 20 mCi.

6. The method of claim 1, wherein said radiation detector device is a gamma ray detector device and said radiation emission is gamma ray emission.

7. The method of claim 6, wherein said gamma ray detector device is a gamma scintillation camera.

8. The method of claim 6, wherein the measuring of gamma ray emission to construct the image is done between about 5 minutes and about 2 hours after administration of the labeled annexin.

9. The method of claim 8, wherein the measuring of gamma ray emission to construct the image is done about 1 hour after administration of the labeled annexin.

10. The method of claim 1, which further includes repeating steps (b) and (c) at selected intervals, wherein said repeating is effective to track changes in the intensity of radiation emission from the region over time.

11. The method of claim 1, which further includes repeating steps (b) and (c) at selected intervals,
wherein said repeating is effective to track changes in the localization of radiation emission in the region over time.

12. The method of claim 1, where said radiation detector device is a 3-dimensional imaging camera.

13. The method of claim 1, where said annexin is annexin V.

14. The method of claim 1, wherein the amount of labeled annexin administered is less than about 300 μg protein/kg.

15. The method of claim 14, wherein the amount of labeled annexin administered is between about 1 μg protein/kg and 10 μg protein/kg.

16. The method of claim 1, wherein the labeled annexin is administered intravenously.

17. The method of claim 1, wherein the labeled annexin is administered intraperitoneally.

18. A method of imaging phosphatidylserine exposure on a nucleated cell within a region of a human subject in vivo, comprising
(a) administering to the human subject, annexin labeled with a biocompatible radionuclide,
(b) measuring radiation emission from the radionuclide in the human subject, to construct an image of radiation emission,
wherein said image is a representation of phosphatidylserine exposure on said nucleated cell within a region of said human subject.

19. The method of claim 18, wherein the radionuclide is selected from the group consisting of Iodine 123, Iodine 131, Gallium 67, Indium 111, Fluorine 18, and Technetium 99 m (Tc99m).

20. The method of claim 19, wherein the radionuclide is technetium 99 m (Tc99m).

21. The method of claim 20, wherein the Tc99m is linked to the annexin via hydrazino nicotinamide (HYNIC).

22. The method of claim 20, wherein the amount of Tc99m-labelled annexin administered results in a dose of between about 5 mCi and about 20 mCi.

23. The method of claim 20, wherein said radiation emission is measured using a gamma ray detector device.

24. The method of claim 23, wherein said gamma ray detector device is a gamma scintillation camera.

25. The method of claim 23, wherein the measuring of gamma ray emission to construct the image is done between about 5 minutes and about 2 hours after administration of the labeled annexin.

26. The method of claim 25, wherein the measuring of gamma ray emission to construct the image is done about 1 hour after administration of the labeled annexin.

27. The method of claim 18, which further includes repeating steps (b) and (c) at selected intervals,
wherein said repeating is effective to track changes in the intensity of radiation emission from the region over time.

28. The method of claim 18, which further includes repeating steps (b) and (c) at selected intervals,
wherein said repeating is effective to track changes in the localization of radiation emission in the region over time.

29. The method of claim 23, where said radiation detector device is a 3-dimensional imaging camera.

30. The method of claim 18, where said annexin is annexin V.

31. The method of claim 18, wherein the amount of labeled annexin administered is less than about 300 μg protein/kg.

32. The method of claim 31, wherein the amount of labeled annexin administered is between about 1 μg protein/kg and 10 μg protein/kg.

33. The method of claim 18, wherein the labeled annexin is administered intravenously.

34. The method of claim 18, wherein the labeled annexin is administered intraperitoneally.

35. The method of claim 18, wherein the labeled annexin is administered intrathecally.

36. The method of claim 18, wherein the labeled annexin is administered intrapleurally.

37. The method of claim 18, wherein the labeled annexin is administered intralymphatically.

38. The method of claim 18, wherein the labeled annexin is administered intramuscularly.

39. The method of claim 1, wherein said region is in an organ of said subject or any portion of the organ.

40. The method of claim 1, where said region is in the head of said subject or any portion of the head.

41. The method of claim 1, where said region is in the heart of said subject or any portion of the heart.

42. The method of claim 1, where said region is in the liver of said subject or any portion of the liver.

43. The method of claim 1, where said region is in the lungs of said subject or any portion of the lungs.

44. The method of claim 1, where said region is in the spleen of said subject or any portion of the spleen.

45. The method of claim 1, where said region is in the bone marrow of said subject or any portion of the bone marrow.

46. The method of claim 18, wherein said region is in an organ of said subject or any portion of the organ.

47. The method of claim 18, where said region is in the head of said subject or any portion of the head.

48. The method of claim 18, where said region is in the heart of said subject or any portion or the heart.

49. The method of claim 18, where said region is in the liver of said subject or any portion of the liver.

50. The method of claim 18, where said region is in the lungs of said subject or any portion of the lungs.

51. The method of claim 18, where said region is in the spleen of said subject or any portion of the spleen.

52. The method of claim 18, where said region is in the bone marrow of said subject or any portion of the bone marrow.

53. The method of claim 1, wherein said radiation detector device is a positron emission detector device.

54. The method of claim 21, wherein said radiation emission is measured using a positron emission detector device.

55. The method of claim 1, wherein said region is in a tumor in said subject or any portion of the tumor.

56. The method of claim 18, wherein said region is in a tumor in said subject or any portion of the tumor.

57. The method of claim 1, wherein said region is in a transplant in said subject or any portion of the transplant.

58. The method of claim 18, wherein said region is in a transplant in said subject or any portion of the transplant.

59. The method of claim 1, wherein said region is in an ischemic site in said subject or any portion of the ischemic site.

60. The method of claim 18, wherein said region is in an ischemic site in said subject or any portion of the ischemic site.

* * * * *

UNITED STATES PATENT AND TRADEMARK OFFICE
CERTIFICATE OF CORRECTION

| | | |
|---|---|---|
| PATENT NO. | : 7,357,915 B2 | Page 1 of 1 |
| APPLICATION NO. | : 10/210986 | |
| DATED | : April 15, 2008 | |
| INVENTOR(S) | : Blankenberg et al. | |

It is certified that error appears in the above-identified patent and that said Letters Patent is hereby corrected as shown below:

Col. 1, lines 11-14, insert as follows:

-- FEDERALLY-SPONSORED RESEARCH OR DEVELOPMENT

This invention was made with Government support under contract HL047151 awarded by the National Institutes of Health. The Government has certain rights in this invention. --

Signed and Sealed this
Second Day of August, 2011

David J. Kappos
*Director of the United States Patent and Trademark Office*